United States Patent
Causevic

(10) Patent No.: US 8,948,860 B2
(45) Date of Patent: *Feb. 3, 2015

(54) FIELD-DEPLOYABLE CONCUSSION DETECTOR

(75) Inventor: Elvir Causevic, Chesterfield, MO (US)

(73) Assignee: BrainScope Company, Inc., Bethesda, MD (US)

( * ) Notice: Subject to any disclaimer, the term of this patent is extended or adjusted under 35 U.S.C. 154(b) by 707 days.

This patent is subject to a terminal disclaimer.

(21) Appl. No.: 12/780,355

(22) Filed: May 14, 2010

(65) Prior Publication Data

US 2010/0222694 A1    Sep. 2, 2010

Related U.S. Application Data

(63) Continuation of application No. 12/041,106, filed on Mar. 3, 2008, now Pat. No. 7,720,530, which is a continuation-in-part of application No. 11/195,001, filed on Aug. 2, 2005, now Pat. No. 7,904,144.

(51) Int. Cl.
  *A61B 5/04*    (2006.01)
  *A61B 5/048*   (2006.01)
  *A61B 5/0484*  (2006.01)
  *A61B 5/00*    (2006.01)

(52) U.S. Cl.
  CPC ............ *A61B 5/048* (2013.01); *A61B 5/0484* (2013.01); *A61B 5/726* (2013.01); *A61B 2560/0431* (2013.01)
  USPC .......................................... 600/545; 600/544

(58) Field of Classification Search
  USPC .................................................. 600/544–545
  See application file for complete search history.

(56) References Cited

U.S. PATENT DOCUMENTS

| | | | |
|---|---|---|---|
| 3,706,308 A | 12/1972 | John et al. |
| 4,913,160 A | 4/1990 | John |
| 5,083,571 A | 1/1992 | Prichep |
| 5,287,859 A | 2/1994 | John |
| 5,384,725 A | 1/1995 | Coiffman et al. |

(Continued)

FOREIGN PATENT DOCUMENTS

| WO | WO 2005/072459 A2 | 8/2005 |
|---|---|---|
| WO | WO 2005/072608 A1 | 8/2005 |

(Continued)

OTHER PUBLICATIONS

Comon, "Independent component analysis, a new concept?," Signal Processing, 36:287-314 (1994).

(Continued)

*Primary Examiner* — Michael D'Angelo
(74) *Attorney, Agent, or Firm* — Finnegan, Henderson, Farabow, Garrett & Dunner, LLP

(57) ABSTRACT

A method and apparatus for providing an on-site diagnosis of a subject to determine the presence and/or severity of a concussion is provided. The method includes placing an electrode set coupled to a handheld base unit on the subject's head, acquiring brain electrical signals from the subject through the electrode set, processing the acquired brain electrical signals using a signal processing algorithm stored in a memory of the base unit, determining the presence and/or severity of a concussion from the processed signals, indicating the presence and/or severity of a concussion on the handheld base unit, and determining a course of treatment for the subject based on the indication.

6 Claims, 3 Drawing Sheets

(56) References Cited

U.S. PATENT DOCUMENTS

| | | | |
|---|---|---|---|
| 5,488,474 | A | 1/1996 | Fateley et al. |
| 5,526,299 | A | 6/1996 | Coifman et al. |
| 6,052,619 | A | 4/2000 | John |
| 6,360,122 | B1 | 3/2002 | Fischell et al. |
| 6,385,486 | B1 | 5/2002 | John et al. |
| 6,654,623 | B1 | 11/2003 | Kästle |
| 6,658,287 | B1 | 12/2003 | Litt et al. |
| 6,866,639 | B2 | 3/2005 | Causevic et al. |
| 7,054,453 | B2 | 5/2006 | Causevic et al. |
| 7,299,088 | B1 * | 11/2007 | Thakor et al. ............... 600/544 |
| 7,302,064 | B2 | 11/2007 | Causevic et al. |
| 7,373,198 | B2 | 5/2008 | Bibian et al. |
| 7,720,530 | B2 * | 5/2010 | Causevic ..................... 600/544 |
| 2002/0039455 | A1 | 4/2002 | Kanamaru et al. |
| 2002/0082514 | A1* | 6/2002 | Williams et al. ............. 600/544 |
| 2002/0091335 | A1 | 7/2002 | John et al. |
| 2002/0095194 | A1 | 7/2002 | Charvin et al. |
| 2003/0013981 | A1 | 1/2003 | Gevins et al. |
| 2003/0181821 | A1 | 9/2003 | Greenweld et al. |
| 2003/0185408 | A1 | 10/2003 | Causevic et al. |
| 2003/0187638 | A1 | 10/2003 | Causevic et al. |
| 2004/0010203 | A1 | 1/2004 | Bibian et al. |
| 2004/0243017 | A1 | 12/2004 | Causevic |
| 2004/0267152 | A1 | 12/2004 | Pineda |
| 2005/0084014 | A1 | 4/2005 | Wang et al. |
| 2005/0113666 | A1 | 5/2005 | Bonmassar et al. |
| 2005/0165327 | A1 | 7/2005 | Thibault et al. |
| 2006/0217632 | A1 | 9/2006 | Causevic et al. |
| 2007/0032737 | A1* | 2/2007 | Causevic et al. ............. 600/544 |
| 2007/0173732 | A1 | 7/2007 | Causevic et al. |
| 2008/0208073 | A1 | 8/2008 | Causevic |
| 2009/0227889 | A2* | 9/2009 | John et al. .................... 600/544 |

FOREIGN PATENT DOCUMENTS

| | | |
|---|---|---|
| WO | WO 2006/034024 | 3/2006 |
| WO | WO 2007/016149 | 2/2007 |
| WO | WO 2007/016149 A2 | 2/2007 |

OTHER PUBLICATIONS

Delorme et al., "Enhanced detection of artifacts in EEG data using higher-order statistics and independent component analysis," NeuroImage 34:1443-1449 (2007).

Hadjileontiadis et al., "Empirical mode decomposition and fractal dimension filter," IEEE Engineering in Medicine and Biology Magazine, Jan./Feb. 2007, pp. 30-39.

Higuchi, "Approach to an Irregular Time Series on the Basis of the Fractal Theory," Physica D 31, (1988), pp. 277-283.

Hyvärinen, "Fast and robust fixed-point algorithms for independent component analysis," IEEE Transactions on Neural Networks 10(3); (1999), pp. 626-634.

Jacquin et al., "Adaptive complex wavelet-based filtering of EEG for extraction of evoked potential responses", Proc. IEEE Int. Conf. Acoust., Speech, and Signal Proc., Philadelphia, PA, Mar. 2005, pp. V:393-V:396.

Jacquin et al., "Optimal denoising of Brainstem Auditory Evoked Response (BAER) for automatic Peak Identification and Brainstem Assessment", Proceedings of the 28th IEEE EMBS Annual Int'l Conference, New York, Aug. 30-Sep. 3, 2006, pp. 1723-1726.

Jung et al., "Removing electroencephalographic artifacts by blind source separation," Psychophysiology 37, (2000), pp. 163-178.

Ksiezyk et al., "Neural networks with wavelet preprocessing in EEG artifact recognition," Laboratory of Medical Physics, Institute of Experimental Physics, Warsaw University, Hoza 69 00 681 Warszawa, Poland, 1998.

Mizrahi et al., "Cerebral concussion in children:assessment of injury by electroencephalogaphy," Pediatrics, 1984 73(4), 419-425.

Nitish V. Thakor and Shanbao Tong, Advances in Quantitative Electroencephalogram Analysis Methods, Annu. Rev. Biomed. Eng., vol. 6, pp. 453-459, Apr. 2, 2004.

Office Action issued May 20, 2010, in corresponding Chinese Application No. 200680032572.1.

Office Action issued May 7, 2010, in corresponding European Application No. 06800351.6.

PCT International Search Report and the Written Opinion mailed Apr. 22, 2008, in related PCT Application No. PCT/US06/28985.

PCT International Search Report and the Written Opinion mailed Jul. 2, 2009, in related International Application No. PCT/US2009/035800.

PCT Search Report and Written Opinion issued by European Patent Office in International Application No. PCT/US2009/040808, mailing date Jul. 31, 2009.

Vorobyov et al., "Blind noise reduction for multisensory signals using ICA and subspace filtering, with application to EEG analysis," Biol. Cybern. 86, 293-303 (2002).

* cited by examiner

FIELD-DEPLOYABLE CONCUSSION DETECTOR

This is a continuation of application Ser. No. 12/041,106, filed Mar. 3, 2009, which is a CIP of application Ser. No. 11/195,001, filed on Aug. 2, 2005, which is incorporated herein by reference.

TECHNICAL FIELD

Embodiments consistent with the present invention relate to the field of emergency triage, and specifically, a portable apparatus and method for performing emergency neurological triage on a subject who has recently suffered a head injury to determine if the subject has a concussion.

BACKGROUND

Objective and sensitive methods to detect subtle brain dysfunction resulting from concussion is needed. According to reports from the U.S. Military, blast concussion brain injury is the most significant proportion of current casualties in Iraq and Afghanistan. However, inadequate preparation and clinical tools to recognize and properly treat such casualties increases the profile of these injuries and their aftereffects. The brain performs the most complex and essential processes in the human body. Surprisingly, contemporary health care lacks sophisticated tools to objectively assess their function. A patient's mental and neurological status is typically assessed clinically by an interview and a subjective physical exam. A typical clinical laboratory currently has no capacity to assess brain function or pathology, contributing little more than identification of poisons, toxins, or drugs that may have externally impacted the CNS. These laboratories can diagnose possible concussions, through the physical exam, but determining the severity of the concussion cannot be done with any accuracy.

Brain imaging studies, such as computed tomography imaging (CT), magnetic resonance imaging (MRI), are widely used and useful. These structural and anatomical tests, however, reveal little information about brain function. The "functional MRI" (fMRI) is a recent improvement over MRI. fMRI testing provides relative images of the concentration of oxygenated hemoglobin in various parts of the brain. While the concentration of oxygenated hemoglobin, which shows the usage of oxygen, is a useful indication of the gross metabolic function of specific brain regions, it provides very limited or no information about the underlying brain function, i.e., the processing of information by the brain, which is electrochemical in nature.

For example, an injured brain part can be using a "normal" amount of oxygen. An fMRI will thus not be able to diagnose a condition or injury which may be dramatically dysfunctional. Moreover, in the immediate time following an acute traumatic brain injury (TBI), such as a concussion, CT and MRI/fMRI imaging studies are typically negative, revealing no structural abnormalities, even when there is clear and dramatically abnormal brain function. The same is also true of diffuse axonal injury (DAI), related to shearing of nerve fibers which is present in the majority of concussive brain injury cases, and can remain invisible on most routine structural images. Swelling or edema from DAI resulting from a concussion can subsequently lead to coma and death.

Further, CT and MRI/fMRI testing devices are completely unavailable in portable, field-deployable applications, due to their size, power requirements and cost. These assessment tools play an important role in selected cases, but they are costly, not universally available, and they do not provide critical information at the early stages of acute care situations. Current technologies are unable to provide the immediate, actionable information critical to timely intervention, appropriate triage, or the formulation of an appropriate plan of care for acute brain trauma such as a concussion. However, the brain has the least capacity for repair among organs, and thus time sensitive triage and intervention is very important in treating brain injuries such as concussions.

All of the brain's activity, whether reflexive, automatic, unconscious, or conscious, is electrical in nature. Through a series of electro-chemical reactions, mediated by molecules called neurotransmitters, electrical potentials (voltages) are generated and transmitted throughout the brain, traveling continuously between and among the myriad of neurons. This activity establishes the basic electrical signatures of the electroencephalogram (EEG) and creates identifiable frequencies which have a basis in anatomic structure and function. Understanding these basic rhythms and their significance makes it possible to characterize the EEG as being within or beyond normal limits. At this basic level, the EEG serves as a signature for both normal and abnormal brain function.

The electrical activity of the brain has been studied extensively since the first recordings over 75 years ago, and especially since the advent of computers. "Normal" electrical activity of the brain has been well characterized in hundreds of studies, with a narrow standard deviation. The frequencies of electrical activity of some parts of the brain are the normal response to various stimuli, such as acoustic, visual, or pain, known as "evoked potentials."

Evoked potentials (EP) are particular waves that have characteristic shapes, amplitudes and duration of peaks within those wave shapes, and many other features, all of which have well established normative data, generated over decades of research. Normative data for all of the EEG and evoked response waves are remarkably constant across different genders, ages, and ethnicities. Moreover, any variability that does exist is well described and explained.

Neuroscientists have also characterized the EEG signature of various different brain pathologies. Just as an abnormal electrocardiogram (ECG) pattern is a strong indication of a particular heart pathology, an irregular brain wave pattern is a strong indication of a particular brain pathology such as concussion. A large body of data, with continuing refinements and contributions, constitutes the field of clinical neurophysiology.

Even though EEG-based neurometric technology is accepted today and a tremendous body of data exists, application in the clinical environment is notably limited. Some of the barriers limiting its adoption include: the cost of EEG equipment, its lack of portability, the need for a technician to administer the test, the time it takes to conduct the test, and the need for expert interpretation of the raw data. More importantly, the technology is neither available nor practical in the acute care setting, especially at the point of care. A complete diagnostic EEG instrument typically costs $80,000, fully equipped. Despite the high costs, the instrument produces essentially raw waveforms which must be carefully interpreted by an expert. Moreover, use of the standard EEG equipment remains extremely cumbersome. It can take 30 minutes or more to apply the required 19 electrodes. Once a subject is prepared for the test, the EEG recording can take from 1 to 4 hours. Data is collected and analyzed by an EEG technician, and is then presented to a neurologist for interpretation and clinical assessment. There are some self-standing dedicated neurodiagnostic laboratories which focus strictly on detailed analysis of electrical brain data. Neither the specialized centers, nor the typically large hospital EEG machines are practical for the ER, operating room (OR), intensive care unit (ICU), or any other acute care medicine setting where patients are in the greatest need.

Studies conducted by medical professionals worldwide have highlighted the need for developing a way to provide an early diagnosis and effective treatment for patients who have suffered a traumatic head injury, in particular, a concussion. Head injuries, such as a concussions, may have serious long term effects. For example, one of the largest threats posed by a concussion is delayed brain swelling caused by fiber shearing, which, if left untreated, can cause coma and death. When properly diagnosed, concussions may be treated using different treatment options, but each of the treatments includes its own risk, and should be administered based on the severity of the injury. Immediate, functional concussion detection is needed to treat patients with possible concussions for the prevention of further damage and disability.

Many times, despite the need for early detection, concussions often go undetected, particularly when a subject is not exhibiting any visible wounds. CT scans and MRI images have less than a 60% accuracy for the detection of a concussion, and are limited in tracking progress of the concussion and guiding treatment. Electrical signals emitted by the brain, however, may be an accurate detector of concussion and its' aftereffects, usually having an accuracy of 90-95%. Moreover, monitoring the brain's electrical signals may also be used to monitor the progress of the concussion over time allowing for excellent treatment management.

SUMMARY

Consistent with the present invention, there is provided a portable device, Brain Concussion Detector using Bx™ technology, for detecting the presence and/or severity of a concussion in a subject, comprising a headset comprising a plurality of brain-electrical-signal-detecting electrodes, and a hand held base unit operably coupled to the headset, the base unit comprising a processor, a memory, the memory containing instructions for causing the processor to perform a signal processing algorithm on the detected signals, and an indicator for providing an indication of the presence and/or severity of a concussion.

Consistent with the present invention, there is also provided a method for providing an on-site diagnosis of a subject to determine the presence and/or severity of a concussion, comprising placing an electrode set coupled to a handheld base unit on the subject's head, acquiring brain electrical signals from the subject through the electrode set, processing the acquired brain electrical signals using a signal processing algorithm stored in a memory of the base unit, determining the presence and/or severity of a concussion from the processed signals, indicating the presence and/or severity of a concussion on the handheld base unit, and determining a course of treatment for the subject based on the indication.

Consistent with the present invention, there is also provided a method for determining if a subject has suffered a recent concussion using a portable handheld device, comprising acquiring brain electrical signals from the subject using an electrode set operably coupled to the handheld device, processing the acquired signals using a signal processing algorithm, determining if the subject has a concussion using the processed signals, and indicating the determination on the portable handheld device.

Consistent with the present invention, there is also provided a portable handheld device, Brain Concussion Detector using Bx™ technology, for detecting the presence and/or severity of a concussion in a subject, comprising a headset comprising a plurality of brain-electrical-signal-detecting electrodes and means for evoking neurological potentials, and a handheld base unit operably coupled to the headset, the base unit comprising a processor, a memory, the memory containing instructions for causing the processor to perform a signal processing algorithm on the detected signals, a display, the display providing a visual display of the presence and/or severity of a concussion, at least one of a video or audio recording device for recording at least one of audio or video of the subject, the memory containing instructions for causing the processor to analyze the recorded at least one of audio or video and extract features from the at least one of audio or video recordings, the extracted features being used by the processor in the signal processing algorithm, and a wireless communication device for transmitting the detected and processed signals to a remote database.

Further consistent with the present invention, there is provided a portable handheld device, Brain Concussion Detector using Bx™ technology, for detecting the presence and/or severity of a concussion in a subject, comprising a headset comprising a plurality of neurological signal-detecting electrodes and means for evoking neurological potentials, and a handheld base unit operably coupled to the headset, the base unit comprising a processor, a memory, the memory containing instructions for causing the processor to perform a signal processing algorithm on the detected signals, and a display, the display providing a visual display of the presence and/or severity of a concussion, wherein the display provides a color-coded indication of the presence and/or severity of a concussion, the color-coded indication comprising a red indication, which is displayed if the concussion is present and serious an orange indication, which is displayed if a concussion is likely present, and more tests are required to be performed on the subject, and a green indication, which is displayed if there is no concussion.

It is to be understood that both the foregoing general description and the following detailed description are exemplary and explanatory only and are not restrictive of the invention, as claimed.

The accompanying drawings, which are incorporated in and constitute a part of this specification, illustrate embodiments consistent with the present invention and together with the description, serve to explain the principles of the invention.

DETAILED DESCRIPTION

Reference will now be made in detail to embodiments consistent with the present the invention, examples of which are illustrated in the accompanying drawings. Wherever possible, the same reference numbers will be used throughout the drawings to refer to the same or like parts.

Collected normative data has been used to establish quantitative features of brain electrical activity which clearly distinguish normal brain function from abnormal dysfunctional conditions. This normative data has been shown to be independent of racial background and to have extremely high test-retest reliability, specificity (low false positive rate) and sensitivity (low false negative rate). Conducted studies of 15,000 normal and pathological evaluations have demonstrated that brain electrical signals are highly sensitive to changes in normal brain function, and change their characteristics instantaneously after catastrophic events such as concussive (blast) or traumatic (impact) brain injuries, ischemia or stroke, and also reflect a variety of chronic developmental, neurological and psychiatric disorders which are not related to any detectable change in physical brain structure. Because different types of brain injuries and diseases affect brain electrical activity in different ways, it is possible to differentiate not only normal from abnormal function, but also to independently determine which kind of pathology is affecting the brain and to what degree, providing guidance on how to restore brain function toward more normal operation. Embodiments consistent with the present invention use this as a basis for providing a diagnosis.

Figure 1:
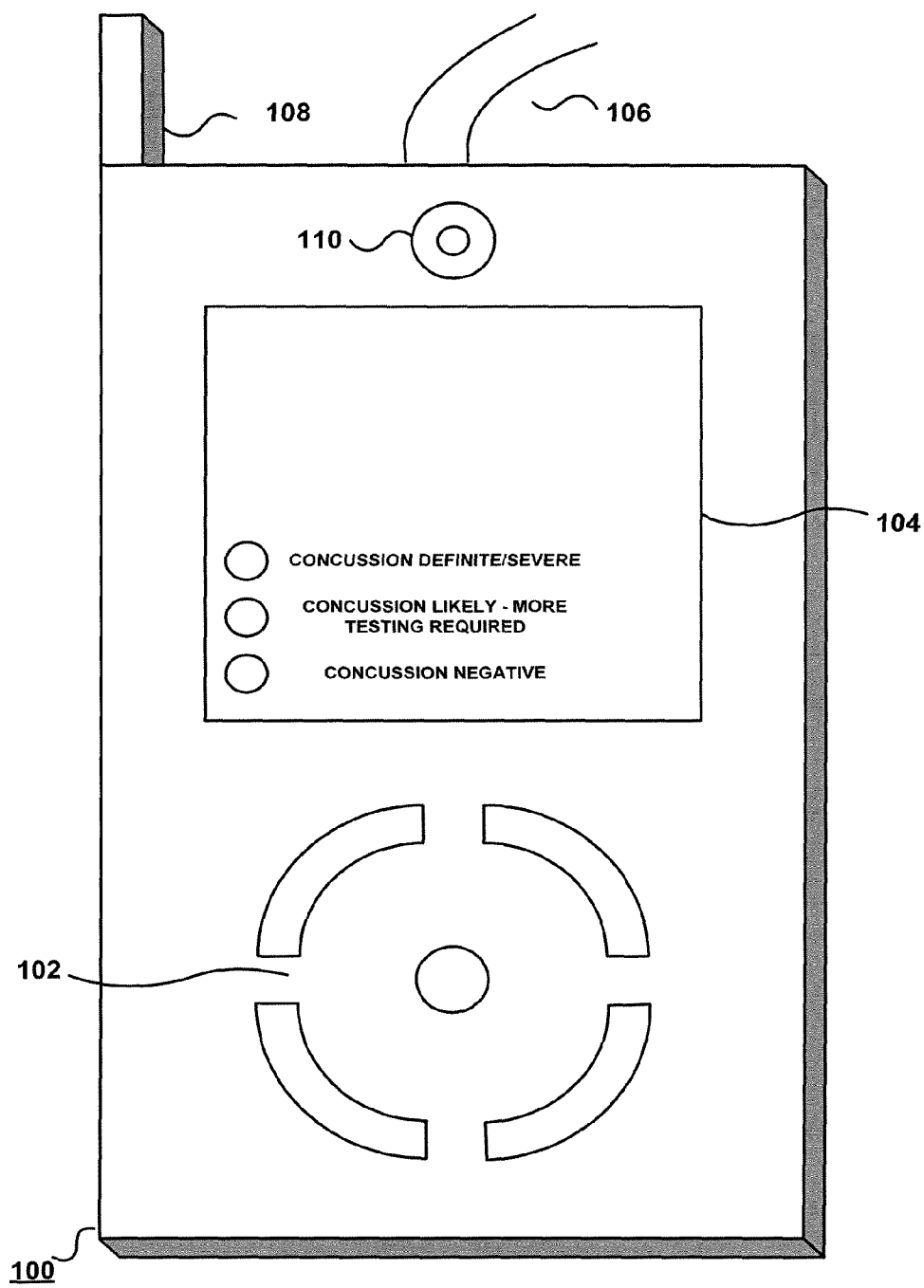
FIG. 1 shows a portable handheld base unit of a concussion detection device consistent with the present invention.

Consistent with the present invention, a portable device, Brain Concussion Detector using Bx™ technology, able to detect a concussion from the brain's electrical signals includes a portable handheld base unit, a headset including a plurality of electrodes connected to the handheld base unit, and software installed on the handheld base unit for, among other things, processing the detected brain signals and determining if a subject has a concussion. FIG. 1 shows the portable handheld base unit of a concussion detection device consistent with the present invention. The portable handheld base unit 100 consistent with the present invention includes a navigation pad 102, which may include a plurality of navigation buttons and a selection button, allowing a user to navigate through menus illustrated on a screen 104, and select options presented on screen 104. Consistent with the present invention, screen 104 may comprise an LCD, LED, OLED, or plasma screen. Screen 104 may also comprise simple LED (or other illumination means) indicators, which provide an indication of, for example, whether the device is on, if tests are being performed, or the presence and/or severity of a concussion.

Consistent with one embodiment of the present invention, the presence and/or severity of a concussion may be indicated using a color-coded light source. A red light source could be illuminated if a concussion is present and serious, an orange light source could be illuminated if a concussion is likely present, but requires more tests to be performed on the subject, and a green light source could be illuminated if there is no concussion. The color-coded indication provides a simple, easy-to-use and easy-to-read means for quickly determining and diagnosing the presence of a concussion in a subject.

Consistent with the present invention, navigation pad 102 may be used to select and execute functions to be performed by handheld base unit 100. For example, screen 104 may display a menu of options highlighting possible options for performing tests on a subject. These options may include beginning testing, selecting the types of tests to perform, and/or options for processing or transmitting acquired data.

Navigation pad 102 may also be used to enter additional information concerning a subject who has suffered a head injury. This additional information includes standard information observed about a subject who has suffered a head injury, including whether the subject is dizzy or unsteady, whether the subject is nauseous or vomiting, whether the subject is unresponsive, and information acquired from the subject in response to interview questions, which could reveal such information as memory loss, loss of vision, ringing in the ears, confusion, or headache. Consistent with an embodiment of the present invention, software stored in a memory of handheld base unit 100 could display on screen 104 a selection screen allowing a user to select the subject's observable features, and information acquired through the interview. Such a selection screen may take the form of a list showing common noticeable features of a concussion, allowing a user to select via a checkbox the observed features.

Handheld base unit 100 may be coupled to a headset (not shown) including a plurality of electrodes via connecting means 106. Connecting means 106 may include a permanently attached or detachable cable or wire, or may include a wireless transceiver, capable of wirelessly transmitting and receiving signals from the headset.

Handheld base unit 100 may also include transceiving antenna 108. Consistent with an embodiment of the present invention, transceiving antenna 108 may be used to wirelessly transmit data stored in the handheld base unit 100 to a remote location for storage or further processing. This data may include diagnosis data, treatment data, or raw electrical signals. The remote location may be a personal computer or a large database. A personal computer may be used for storing and further processing acquired data, allowing, for example, a medical professional to monitor the progress of a subject through the treatment of a concussion. A remote database may be used for storing the acquired data, to allow the acquired data to be added to a larger data pool of subjects having similar brain electrical signals. This larger data pool may be used for neurometric studies to provide a more accurate diagnosis on the basis of comparison.

Handheld base unit 100 may further include an audio/visual data receiving means 110. Audio/visual receiving means 110 may comprise a camera (still/video, or both) and/or a microphone. Consistent with the present invention, in addition to obtaining brain electrical signals through the headset, additional data about the subject may be acquired using audio/visual receiving means 110. This data may include video data showing the subject's facial expressions, eye movement, and balance, and/or audio data including the subject's responses to questions given during a post-injury interview exam revealing a subject's slurred speech or loss of memory. Specific, recognizable features to be extracted from this additional audio/visual data may be used in conjunction with acquired brain electrical signals to provide a diagnosis of a subject, and determine if the subject suffered a concussion.

Further consistent with the present invention, software stored in a memory of handheld base unit 100 may be configured to display on screen 104 results of the testing. Results may include displaying a brain map generated from the acquired data showing an indication of a brain injury, a location of a brain injury, or a severity of a brain injury. Results may also include a simple indication of a concussion. The simple indication may comprise a red/orange/green light source as described above, or may be a simple text display indicating the presence and/or severity of a concussion.

Software stored in a memory of handheld base unit 100 may further be configured to display on screen 104 additional information related to the testing of a subject or the operation of the device. For example, memory may contain interactive instructions for using and operating the device to be displayed on screen 104. The interactive instructions may comprise a feature-rich presentation including a multimedia audio/video recording providing visual and audio instructions for operating the device, or may simple be a text file, displayed on screen 104, illustrating step-by-step instructions for operating and using the device. The inclusion of interactive instructions with the device eliminates the need for a device that requires extensive training to use, allowing for deployment and use by non-medical professionals.

Figure 2:
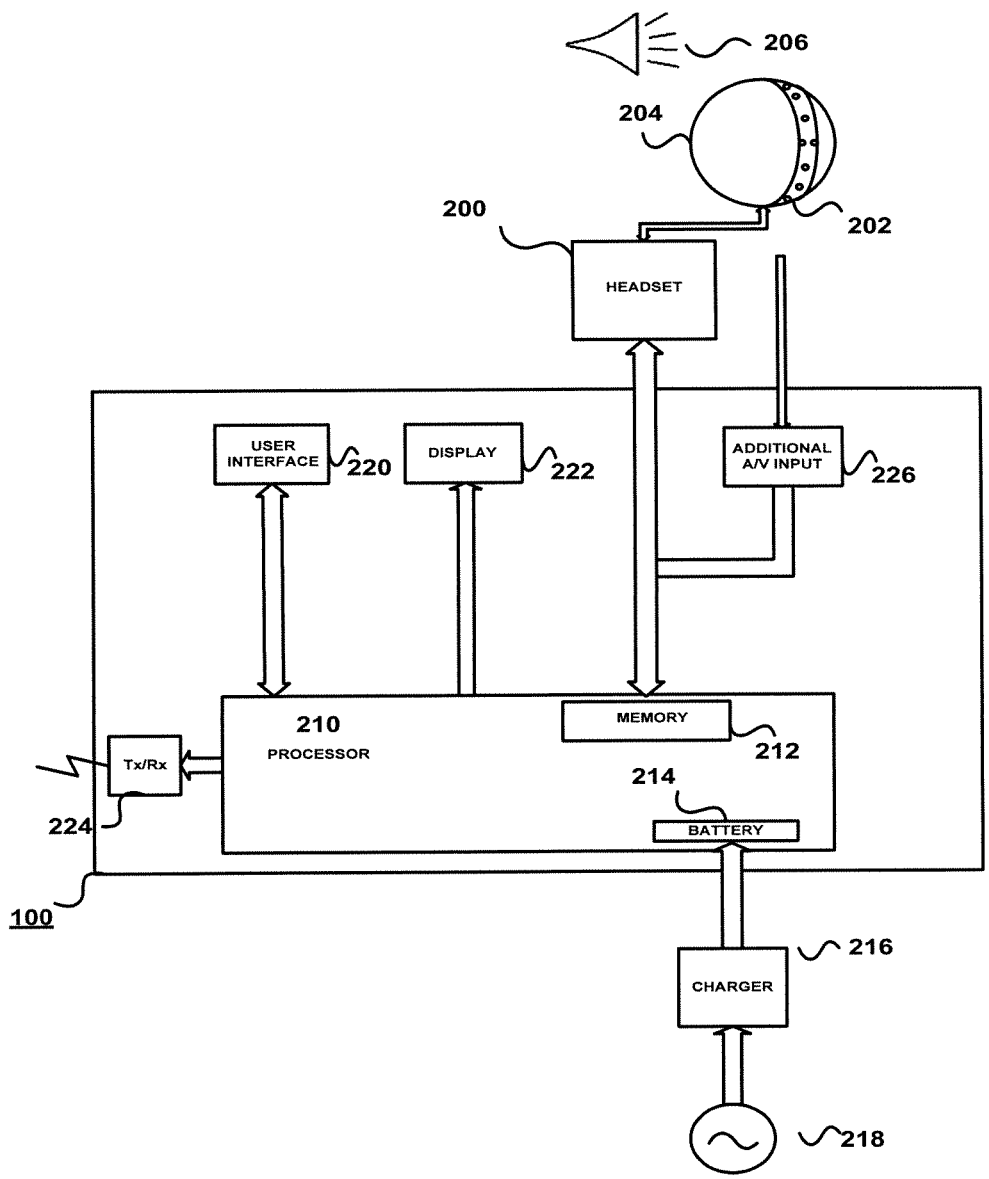
FIG. 2 shows a schematic diagram of the portable handheld base unit consistent with the present invention.

FIG. 2 shows a schematic diagram of portable handheld base unit 100 consistent with the present invention. As shown in FIG. 2, handheld base unit 100 is connected to headset 200. Headset 200 may include an electrode set 202 for detecting brain electrical signals to be placed on a subject's head 204. Electrode set 202 may comprise a reduced electrode set, having less than 19 electrodes, and preferably less than 10 electrodes. Headset 200 may also include a stimulus emitter 206 to be used for evoked potential tests. Stimulus emitter 206 may include an audio or visual stimulus emitter.

Handheld base unit 100 also includes an electronics block 208 including processor 210, memory 212, and a power source 214 for providing power to the electronics block. In one embodiment consistent with the present invention, power source 214 comprises a rechargeable battery, which can be recharged when coupled to a charger 216 being powered by an AC or DC power source 218.

Electronics block 208 is further coupled to headset 200, user interface electronics 220 for controlling, for example, navigational pad 102, display electronics 222 for controlling, for example, screen 104, and consistent with an embodiment of the present invention, wireless electronics 224 for controlling, for example, wireless transceiver 108 and/or a wireless connection 106 to headset 200. Electronics block 208 is also coupled additional A/V electronics 226 for controlling, for example, A/V receiving means 110. In general, memory 212 contains instructions for causing processor 210 to perform functions for operating portable handheld device 100, including all of the electronics illustrated in FIG. 2, and for performing tests on a subject and providing a diagnosis based on the performed tests, as will be described in greater detail.

Figure 3:
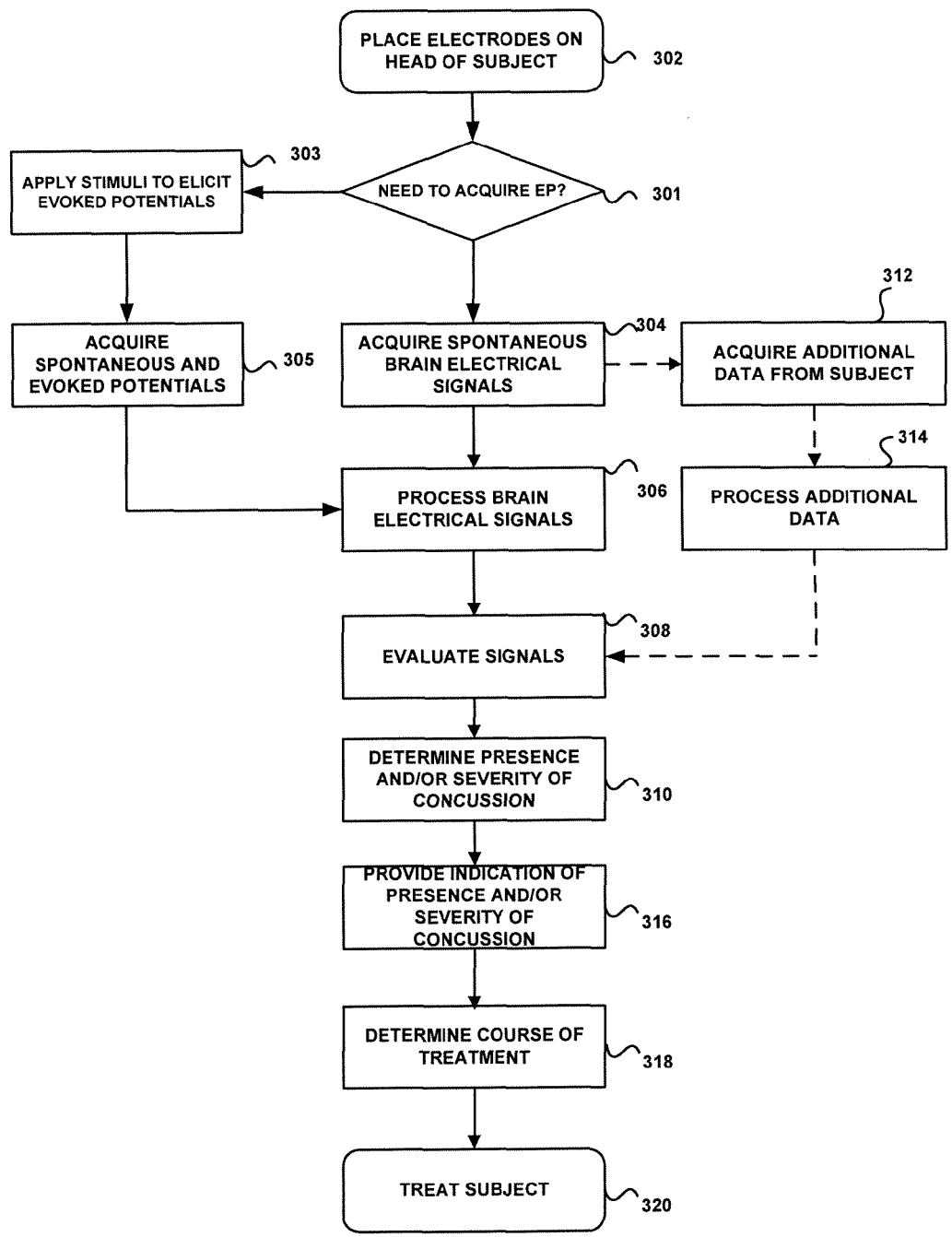
FIG. 3 shows a flowchart diagramming the steps of providing an on-site diagnosis of a patient believed to have a concussion consistent with the present invention.

FIG. 3 shows a flowchart diagramming the steps of providing an on-site diagnosis of a patient believed to have a concussion consistent with the present invention, and will be described in conjunction with FIG. 2 to illustrate a method for providing a diagnosis consistent with an embodiment of the present invention. Electrodes 202 are first placed on the head of a subject 204 who has just received a head injury and may have a concussion (step 302). Handheld base unit 100 is powered on using power supplied from battery 214, and processor 210 executes instructions stored in memory for controlling display electronics 222 to display information including a power state, a readiness state, a testing mode, and/or a message for the user to enter a command. A user then uses navigation pad 102 to enter a command to start the testing. If the user determines that evoked potentials may also have to be recorded (step 301), he may initiate stimulus emitter 206 and apply stimuli to the brain to elicit evoked potentials (step 303). User interface electronics passes the user command to electronics block 208, and processor 210 interprets the command and provides a signal to headset electronics to begin acquiring signals. Brain electrical signals, which may include at least one of spontaneous or evoked potentials are acquired from headset electrodes 202 (step 304 or step 305) and passed from headset electronics to electronics block 208 for processing. Processor 210 then executes instructions contained in memory 212 for processing the acquired signals (step 306).

In an embodiment consistent with the present invention, the signals are processed to remove noise, processed to extract features, and processed to classify the extracted features. More specifically, memory 212 can contain instructions that are executed by the processor 210 which for processing the signals using a Dual-Tree Complex Wavelet Transform as an invertible transform to adaptively filter the acquired signals. The instructions further may contain an implementation of an algorithm carried out by processor 210, wherein a complex wavelet transform is computed for each sub-average, and then the phase variance of each normalized wavelet coefficient $w_{i,j}$ is computed. The magnitude of each wavelet coefficient is selectively scaled according to the phase variance of the coefficients at this location across the sub-averages. The scaling has the form:

$$w_{i,j} = \alpha_{i,j} W_{i,j} \exp(j\theta_{i,j}),$$

where $W_{i,j}$ and $\theta_{i,j}$ are respectively the magnitude and phase of the unprocessed complex $i^{th}$ wavelet coefficient at the $j^{th}$ scale, and where:

$$\alpha_{i,j} = \exp(-0.75(F_{ij}/T_{max})^4,$$

where $F_{ij}$ is the phase variance of coefficient $w_{ij}$ across the sub-averages. The filtered signals are averaged and an automatic peak detection algorithm is implemented by processor 210 to determine the following peak locations and latencies: Peak 1, Peak 2, and Interpeak 1-5 latency. These values are then compared by processor 210 to normative data contained in memory 212.

In an embodiment consistent with the present invention, processing the signals may comprise performing an algorithm for removing noise from the acquired signals, or "denoising." In one embodiment, the denoising algorithm utilizes wavelet-based signal processing using wavelet transforms. In other embodiments, the algorithm may comprise a diffusion geometry processing algorithm or a fractal processing algorithm. The wavelet transform, a member of the family of Fourier transforms, is a process of decomposing a given signal into a set of orthonormal basis functions called wavelets. In traditional discrete Fourier transform (DFT), a signal is decomposed using complex sinusoids as basis functions, producing a frequency domain representation of the signal. In contrast, a discrete wavelet transform (DWT) uses a family of specifically designed wavelets, or little waves, as basis functions. A family of wavelets is created by dilating the original wavelet function, termed the "mother wavelet." A wavelet transform decomposes the signal in both time and frequency using different dilations of the mother wavelet. With the application of DWT, the one dimensional finite signal x[n] is represented in two-dimensional "wavelet coordinates." Individual levels of signal decomposition are created, called scales. At each scale a set of coefficients is created by computing the inner product of the original signal x[n] with a scaled version of the mother wavelet. The mother wavelet function is designated by $\Psi$, and its dilations are designated by $\Psi(j)$. The position index of a wavelet at scale j is called a translation. The value of the wavelet is completely described by the two dimensional sequence $\Psi(j,k)$, where j is the scale index of the wavelet, and k is the translation index. The DWT is the defined as:

$$C(j,k) = \sum_{n=0}^{N-1} x[n]\Psi_{j,k}[n], \text{ where } \Psi_{j,k}[n] = 2^{\frac{-j}{2}}\Psi(2^{-j}n-k)$$

Coefficients C(j,k) are the wavelet coefficients at different scales j and translations k of the inner product of the wavelet Y(j,k) with the original signal x[n]. In wavelet coordinates, information about both the frequency and the location (time) of the signal energy is preserved. This is a process of noise suppression that utilizes assumptions about smoothness and coherence properties of both the underlying signal and the noise that contaminates it. Similar to filtering in the frequency domain, the wavelet coefficient thresholding algorithm reduces sets of wavelet coefficients in the wavelet domain. This process is based on the assumption that the underlying signal is smooth and coherent, while the noise that is mixed with the signal is rough and incoherent. Smoothness of a signal is a property related to its bandwidth, and is defined in relation to how many times a signal can be differentiated. The degree of smoothness is equal to the number of continuous derivatives that can be calculated. A signal is coherent if its energy is concentrated in both time and frequency domains. An incoherent noise is "spread out," and not concentrated. One measure of coherence is how many wavelet coefficients are required to represent 99% of the signal energy. A time-frequency signal space is completely spanned by wavelet coefficients at all scales and translations. A well-concentrated signal decomposition in an appropriately selected wavelet basis will require very few coefficients to represent 99% of signal energy. However, a completely incoherent noise will require 99% of the coefficients that span the entire space to represent 99% of its energy.

This conventional wavelet denoising process is a three step process:
1. Wavelet transform the signal to obtain wavelet coefficients at different scales
2. Threshold the coefficients and set to zero any smaller than a threshold δ
3. Perform the inverse wavelet transform to approximate the original signal In the denoising process, the noise components of the signal are attenuated by selectively setting the wavelet coefficients to zero. Denoising is thus a non-linear operation, because different coefficients are affected differently by the thresholding function. There are many parameters to control in this algorithm: level of wavelet decomposition, threshold selection, using different thresholds at different wavelet coefficients that are kept by a fixed amount.

Consistent with an embodiment of the present invention, the denoising process involves dividing the acquired signals into discrete intervals, or "frames," and then averaging the frames, and denoising the averaged frames. The greater amount of frames that are denoised prior to recomposing the signal, the better the results of the denoising process. Preferably, the frames are combined by using two adjacent frames and calculating their linear average. This method is chosen for its simplicity, computational stability, and well-understood behavior. This dyadic linear average is then denoised, and a new frame is created. The overall idea is to generate as many permutations of the original arrangement of frames as possible, and keep averaging and denoising those new combinations of frames. This recombination process is a tree-like process, and may comprise the dual-tree process described above, in which new levels of recombined frames are created. The average and denoise operation creates frames at level k, which are no longer a linear combination of frames from level k−1.

The many possible algorithms to accomplish this task can be evaluated by different criteria: ease of implementation, computational efficiency, computational stability, etc. For the present invention, ease of implementation is used, because the key aspect of the invention is implementation of different wavelet denoising techniques and not combinatorics of frame rearrangements. The goal of the preferred embodiment in frame rearranging is to produce enough new frames to obtain acceptable performance.

Processor 210 is further configured to execute instructions contained in memory 212 to perform an algorithm for extracting signals from processed signals to evaluate the processed signals (step 308). In one embodiment, processor 210 executes instructions which performs a feature extraction algorithm on the processed signals according to a method disclosed in U.S. Pat. Nos. 6,358,486, 6,052,619 and 5,287,859, which are incorporated herein by reference. The algorithm utilizes Fast Fourier Transform (FFT) Analysis is applied to characterize the frequency composition of the processed signals, typically dividing the signals into the traditional frequency bands: delta (1.5-3.5 Hz), theta (3.5-7.5 Hz), alpha (7.5-12.5 Hz), beta (12.5-25 Hz), and gamma (25-50 Hz). Higher EEG frequencies, up to and beyond 1000 Hz may also be used. These features can include characteristics of the processed signals such as absolute and relative power, symmetry, and coherence. In the context of analyzing process brainwaves, absolute power is the average amount of power in each frequency band and in the total frequency spectrum of the processed signals, and is a measure of the strength of the brain's electrical activity. Relative power is the percentage of the total power contributed for a respective electrode and a respective frequency band and is a measure of how brain activity is distributed. Symmetry is the ratio of levels of activity between corresponding regions of the two brain hemispheres in each frequency band and is a measure of the balance of the observed activity. Coherence is the degree of synchronization of electrical events in corresponding regions of the two hemispheres and is a measure of the coordination of the brain activity. These four basic categories of univariate features, resulting from the spectral analysis of the process signals, are believed to characterize independent aspects of brain activity and each is believed to be sensitive to a variety of different clinical conditions and changes of state. A full set of individual and pairwise features is calculated and transformed for Gaussianity using, for example, the log function. Once a Gaussian distribution has been demonstrated and age regression applied, statistical Z transformation is performed. The Z-transform is used to describe the deviations from age expected normal values:

$$Z = \text{Probability that subject value lies within the normal range}$$

$$Z = \frac{\text{Subject Value} - \text{Norm for Age}}{\text{Standard Deviation for Age}}$$

The significance of the Z-transform is that it allows measures with different metrics to be combined using the common metric of probability. Using a database of acquired brain electrical signals from a large population of subjects believed to be normal, or to have other conditions, the distribution of these response signals is determined for each electrode in electrode set 202. In particular, each extracted feature or factor score is converted to a Z-transform score, or factor Z-score which characterizes the probability that the extracted feature value or factor score observed in the subject will conform to a normal value.

Processor 210 is further configured to perform an algorithm wherein the extracted features, or the Z-scores are classified to determine the presence and/or severity of a concussion (step 310). In one embodiment, these sets of univariate data is subjected to Gaussian normalization in order to improve the accuracy of any subsequent statistical analysis. The Z-scores are given a selected discriminant score. Each discriminant score is a respective weighted combination of a selected subset of Z-scores for monopolar and/or bipolar univariate and multivariate features derived from the processed signals of a subject. The processor 210 executes an algorithm wherein a respective discriminant score is evaluated for each of two or more diagnostic categories multiplying each of several selected Z-scores by a respective coefficient and adding the resulting products. The coefficients typically differ as between diagnostic categories and as between Z-scores. The probability is evaluated that the subject belongs to one of the two or more diagnostic categories through a probability evaluating expression which is a function of the relevant discriminant scores, matching results against limits provided by memory 212 for the presence and/or severity of a concussion. The diagnostic categories may be indicative of whether a subject has a concussion, the severity of the concussion, and whether or not the concussion requires immediate medical attention.

Consistent with the present invention, a user may also acquire additional data from the subject (step 312). As further discussed above, such additional data may include video data acquired by A/V electronics 226 showing the subject's facial expressions, eye movement, and balance, and/or audio data including the subject's responses to questions given during a post-injury interview exam revealing a subject's slurred speech or loss of memory. At the time of enrollment, information may also be collected from the subject using a symptom checklist, and a health questionnaire about concussion history, severity and frequency of previously diagnosed concussions. As known in the prior art, the symptom checklist can be used to rate the severity of each symptom for the current as well as previously sustained head injuries, and the severity ratings can be summed to provide an overall grade for each concussion suffered. This information about concussion grade and the frequency of concussion may be entered into the processor 210 by the user. A Concussion Index can then be generated by the processor 210 by multiplying the grade of each concussion by the frequency of that type of concussion, and in the case of multiple concussions of different grades, summing these products together. A Concussion Index for each concussed patient may be stored in the memory 212 and may also be wirelessly transmitted to a remote database to serve as an electronic record of the injury. This additional data can be processed by processor 210, along with the A/V data (step 314) and used in conjunction with the processed acquired brain electrical signals to provide an evaluation of the acquired signals (step 308) and determine the presence and/or severity of the head injury (step 310).

Following the determination of the presence and/or severity of a head injury, processor 210 executes instructions to provide an indication of the presence and/or severity of a head injury (step 316) to be displayed by display electronics 222. The indication may comprise a color-coded indication, a brain map, or a simple message displayed on screen 104, as further described above. Processor 210 may then execute an algorithm for determining a course of treatment based on the indication, the processed signals and Concussion Index stored in memory 212 (step 318). For example, using the classification techniques described above, processor 210 may compare the specific indication, the Concussion Index and associated acquired signals to data stored in memory, the data further indicating treatments applied and its success thereof. The stored data may further include information relating to the progression of a specific subject's concussion over time, and the effectiveness of certain treatments applied at a time interval. In executing the algorithm for determining a course of treatment, processor 210 may take all of this information into account in order to narrowly tailor a course of treatment for the subject based on the subject's brain signals. The subject then may be treated (step 320).

Embodiments consistent with the present invention, using advanced signal processing algorithms and stored data of the brain electrical signals of thousands of subjects having concussions and similar brain injuries, may provide a rapid and accurate indication if a subject has a concussion. Moreover, the advanced signal processing algorithms may be executed by a processor capable of integration in a portable handheld device. The portable handheld device used with a reduced electrode set allows for a rapid, portable solution for determining if a subject has a concussion, and determining a course of treatment, and may enable for the early indication of severe concussions, allowing treatment to be given at an early stage of injury.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A portable device for detecting the presence and severity of a concussion in a subject, comprising:
   a headset comprising a plurality of brain-electrical-signal-detecting electrodes, the headset configured to acquire brain electrical signals from the subject; and
   a portable base unit operably coupled to the headset, the base unit comprising:
   a processor;
   a memory, the memory containing instructions for causing the processor to perform, at least in part, a signal processing algorithm on the acquired signals, the signal processing algorithm comprising extraction of signal features from the acquired brain electrical signals and classification of the extracted features into diagnostic categories, wherein the processor is configured to determine the presence and severity of the concussion based on the classification result; and
   an indicator for providing an indication of the presence and severity of the concussion.

2. The portable device according to claim 1, wherein the acquired signals comprise at least one of spontaneous or evoked signals.

3. The portable device according to claim 1, wherein the signal processing algorithm comprises at least one of a wavelet, a wavelet packet processing algorithm, a diffusion geometry processing algorithm, or a fractal processing algorithm.

4. The portable device according to claim 1, wherein the indicator comprises a visual display.

5. The portable device according to claim 4, wherein the visual display comprises:
   a first indicator, which is displayed if concussion is determined to be present and serious;
   a second indication, which is displayed if concussion is determined to be likely present, and more tests are required to be performed on the subject; and
   a third indication, which is displayed if there is no concussion detected.

6. A portable handheld device for detecting the presence and severity of concussion in a subject, comprising:
   a headset comprising a plurality of neurological signal-detecting electrodes and means for evoking neurological potentials; and
   a handheld base unit operably coupled to the headset, the base unit comprising:
   a processor;
   a memory, the memory containing instructions for causing the processor to perform, at least in part, a signal processing algorithm on the detected signals, wherein the processor is configured to determine the presence and severity of concussion based on the detected signals from a single recording session; and a display, the display providing a visual display of the presence and severity of a concussion comprising:

a first indication, which is displayed if concussion is determined to be present and serious;

an second indication, which is displayed if concussion is determined to be likely present, and more tests are required to be performed on the subject; and a third indication, which is displayed if there is no concussion determined to be present.

* * * * *